United States Patent
Ein-Gal

(10) Patent No.: US 7,894,573 B2
(45) Date of Patent: Feb. 22, 2011

(54) NON-RECUMBENT RADIOTHERAPY

(76) Inventor: Moshe Ein-Gal, 30 Azar Street, Ramat Hasharon, 47203 (IL)

( * ) Notice: Subject to any disclaimer, the term of this patent is extended or adjusted under 35 U.S.C. 154(b) by 104 days.

(21) Appl. No.: 12/429,192

(22) Filed: Apr. 24, 2009

(65) Prior Publication Data

US 2010/0272237 A1    Oct. 28, 2010

(51) Int. Cl.
*A61N 5/10* (2006.01)
(52) U.S. Cl. .......................................... 378/65
(58) Field of Classification Search ............... 378/37, 378/65, 196, 197, 204, 207, 208
See application file for complete search history.

(56) References Cited

U.S. PATENT DOCUMENTS

| | | | | |
|---|---|---|---|---|
| 4,691,333 | A * | 9/1987 | Gabriele et al. | 378/37 |
| 5,289,520 | A * | 2/1994 | Pellegrino et al. | 378/37 |
| 5,386,447 | A * | 1/1995 | Siczek | 378/37 |
| 6,298,114 | B1 * | 10/2001 | Yoda | 378/37 |
| 6,418,188 | B1 * | 7/2002 | Broadnax | 378/37 |
| 6,463,122 | B1 * | 10/2002 | Moore | 378/65 |
| 6,577,702 | B1 * | 6/2003 | Lebovic et al. | 378/37 |
| 6,702,806 | B2 * | 3/2004 | Gray et al. | 606/5 |
| 6,987,831 | B2 * | 1/2006 | Ning | 378/37 |
| 7,492,858 | B2 * | 2/2009 | Partain et al. | 378/37 |
| 7,496,174 | B2 * | 2/2009 | Gertner et al. | 378/65 |

* cited by examiner

*Primary Examiner*—Allen C. Ho
(74) *Attorney, Agent, or Firm*—Dekel Patent Ltd.; David Klein

(57) ABSTRACT

A method for radiotherapy of a non-recumbent patient, including immobilizing a region containing a target determining a spatial position of the target in a non-recumbent treatment position by applying a formula to images acquired by recumbent-only imaging in a recumbent position and by general imaging in a non-recumbent position, the formula calculating the non-recumbent treatment position as a function of the target position relative to anatomical and/or other markers as calculated from recumbent-only imaging, and the position of the markers relative to a treatment device as calculated from general imaging in the non-recumbent position, positioning the patient for treatment in the non-recumbent treatment position according to the markers' position, and irradiating the target with a radiation beam while the target is in the non-recumbent treatment position.

10 Claims, 2 Drawing Sheets

NON-RECUMBENT RADIOTHERAPY

FIELD OF THE INVENTION

The present invention generally relates to radiotherapy systems, and more particularly to a radiotherapy system for irradiating a non-recumbent upright patient (e.g., in an upright position or in a forward-leaning position).

BACKGROUND OF THE INVENTION

Advanced radiotherapy requires precise imaging for treatment planning. Since the imaging and the treatment take place at different times and/or locations, patient positions must be maintained as identical as possible in the two procedures to reduce positional errors associated with internal organ displacement and deformation. Patient rotation about a vertical rotational axis is acceptable since such a rotation has no effect on the gravitational forces applied to the internal organs and thus no effect on organ displacement and deformation. Similarly, the patient may be translated relative to a radiation beam but remain in the same position relative to the gravitational field.

Treating a non-recumbent patient, e.g., in an upright position or in a forward-leaning position, may have clinical and economic advantages. However, since the CT scanners used for treatment planning are structurally limited with respect to positioning the patient in a non-recumbent position, such a position is practically not considered in the prior art and CT scanning is performed in the recumbent position. Recumbent-only imaging, e.g., CT or MRI are typically applied in a generally recumbent position, while general imaging e.g., x-ray or ultrasound may be also applied in a non-recumbent position. Typically, recumbent-only imaging provides three dimensional resolution and/or the anatomical details superior to those provided by general imaging. Therefore, treatment planning for radiotherapy is based on recumbent-only imaging.

SUMMARY OF THE INVENTION

The present invention seeks to provide an improved radiotherapy system for irradiating a non-recumbent patient, as is described more in detail hereinbelow.

There is thus provided in accordance with an embodiment of the present invention a method for radiotherapy of a non-recumbent patient, including immobilizing a region containing a target determining a spatial position of the target in a non-recumbent treatment position by applying a formula to images acquired by recumbent-only imaging in a recumbent position and by general imaging in a non-recumbent position, the formula calculating the non-recumbent treatment position as a function of the target position relative to anatomical and/or other markers as calculated from recumbent-only imaging, and the position of the markers relative to a treatment device as calculated from general imaging in the non-recumbent position, positioning the patient for treatment in the non-recumbent treatment position according to the markers' position, and irradiating the target with a radiation beam while the target is in the non-recumbent treatment position.

Immobilizing the region may include encapsulating and compressing the region containing the target. Positioning the patient may include orienting the region through at least two azimuthal or two elevation angles. Additionally or alternatively, positioning the patient may include target localization via imaging.

Irradiating the target may include applying a generally horizontal radiation beam.

The formula may be based on a linear model, wherein the non-recumbent target position relates to the recumbent target position by a shift and rotation determined by gravitational and other forces, wherein target position is relative to the markers.

For rigidly encapsulated regions (such as the brain), the shift and the rotation may be minute. Examples of the region include at least one of a pelvic region, a breast, and a skull.

There is also provided in accordance with an embodiment of the invention, a radiotherapy system for a non-recumbent patient including an immobilizer operable to immobilize a region containing a target so that region deformation is characterized by a formula, wherein the region deformation is the relative position of the region tissue in a recumbent position and in a non-recumbent position, respectively, an imaging device attachable to the immobilizer for imaging the target, a treatment device attachable to the immobilizer for performing treatment of the target in a non-recumbent position, and a processor operable to produce treatment simulation of the region in the non-recumbent position using a formula applied to an image acquired in the imaging position.

The immobilizer may be operable to encapsulate and to compress the region.

BRIEF DESCRIPTION OF THE DRAWINGS

The present invention will be understood and appreciated more fully from the following detailed description, taken in conjunction with the drawing in which.

DETAILED DESCRIPTION OF EMBODIMENTS

Figure 1A:
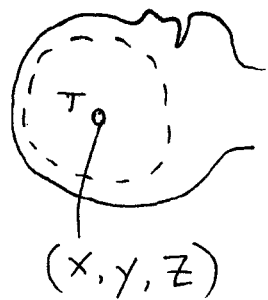
FIGS. 1A and 1B are simplified illustrations of an organ/tissue/target in a recumbent position for imaging and in a non-recumbent position for treatment, respectively.
Figure 1B:
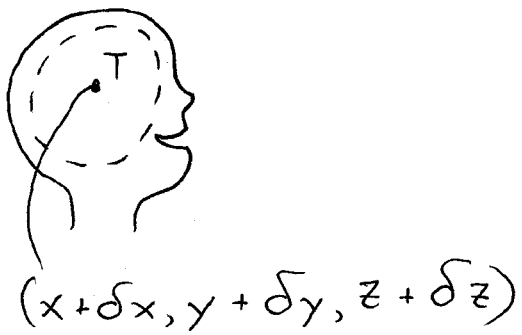

Sagging of encapsulated biological tissue is generally considered to be insignificant. Consequently, rigidly encapsulated tissue is generally insensitive to the orientation of the gravitational force. Such is the case, for example, of the encapsulated brain, as is seen in FIGS. 1A and 1B. FIG. 1A shows the brain with the patient in the recumbent position. A target T has coordinates, such as Cartesian coordinates (x, y, z), with the z-axis being directed along the force of gravity. Despite the encapsulation of the brain, minor brain displacement relative to the skull may nevertheless take place in response to different skull orientations in the gravitational force field. Accordingly, in the non-recumbent position shown in FIG. 1B, the position of target T has changed and is now (x+δx, y+δy, z+δz). It is noted, however, that δx and δy can generally be considered zero. The δz displacement is small and can be modeled, for example, by non-CT brain imaging in the relevant orientations. Such a model provides a formula for displacements in various positions. The formula can be applied to recumbent CT images in order to derive treatment simulation in the non-recumbent position.

Figure 2:
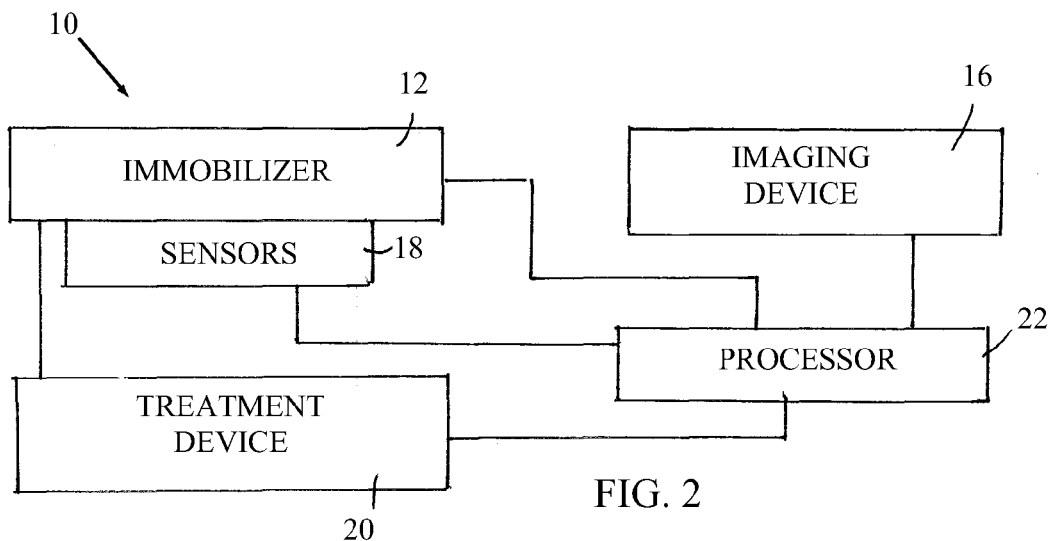
FIG. 2 is a simplified bock diagram of a system for tissue immobilization, constructed and operative in accordance with an embodiment of the present invention.
Figure 3A:
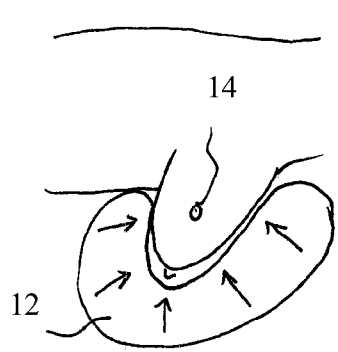
FIGS. 3A and 3B are simplified illustrations of an extra-cranial organ/tissue/target (e.g., female breast) in a recumbent position for imaging and in a non-recumbent position for treatment, respectively.
Figure 3B:
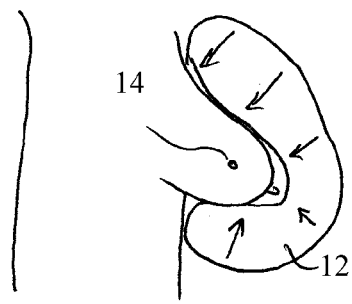

Other organs, such as the female breast, are not encapsulated by bone but are external and readily lend themselves to compression or immobilization. Reference is now made to FIG. 2, which illustrates a system 10 for tissue immobilization, constructed and operative in accordance with an embodiment of the present invention. System 10 includes an immobilizer 12, such as a receptacle for receiving therein the tissue or organ. The receptacle may be made of a rigid material (metal or plastic, for example) and custom-sized to the particular breast, or may include an inflatable balloon that when inflated presses and immobilizes the breast. As seen in FIGS. 3A and 3B, immobilizer 12 immobilizes a region containing a target (in the illustrated case, a target 14 in the breast). The immobilizer 12 may encapsulate and to compress the region. FIG. 3A shows the breast in the imaging (recumbent) position, and FIG. 3B shows the breast in the treatment (non-recumbent) position.

The immobilizer 12 is attached to an imaging device 16, such as but not limited to, an ultrasound imager, X-ray imager, MRI imager and the like, for imaging the region and target in the imaging position of FIG. 3A. The spatial position of immobilizer 12 with respect to the imaging device 16 is known and the spatial movement (translation and rotation) of the immobilizer 12 together with the target is easily sensed and measured by sensors 18, such as by optical means sensing fiducial marks on the immobilizer 12, or by sensors (e.g., accelerometers) mounted on the immobilizer 12 or by any other means. The immobilizer 12 is also attachable, either separately or simultaneously, to a treatment device 20, such as but not limited to, a LINAC, for performing treatment in the non-recumbent position of FIG. 3B. Again, the spatial position and movement of immobilizer 12 with respect to the treatment device 20 is known.

The region deformation is the relative position of the region tissue in the imaging position (FIG. 3A) and in the non-recumbent treatment position (FIG. 3B), respectively. The region deformation may be characterized by a formula, which takes into account the tissue elasticity and other parameters. A processor 22, operatively connected to immobilizer 12, sensors 18, imaging device 16 and treatment device 20, produces a treatment simulation of the region in the non-recumbent position using a formula applied to an image acquired in the imaging position.

Figure 4:
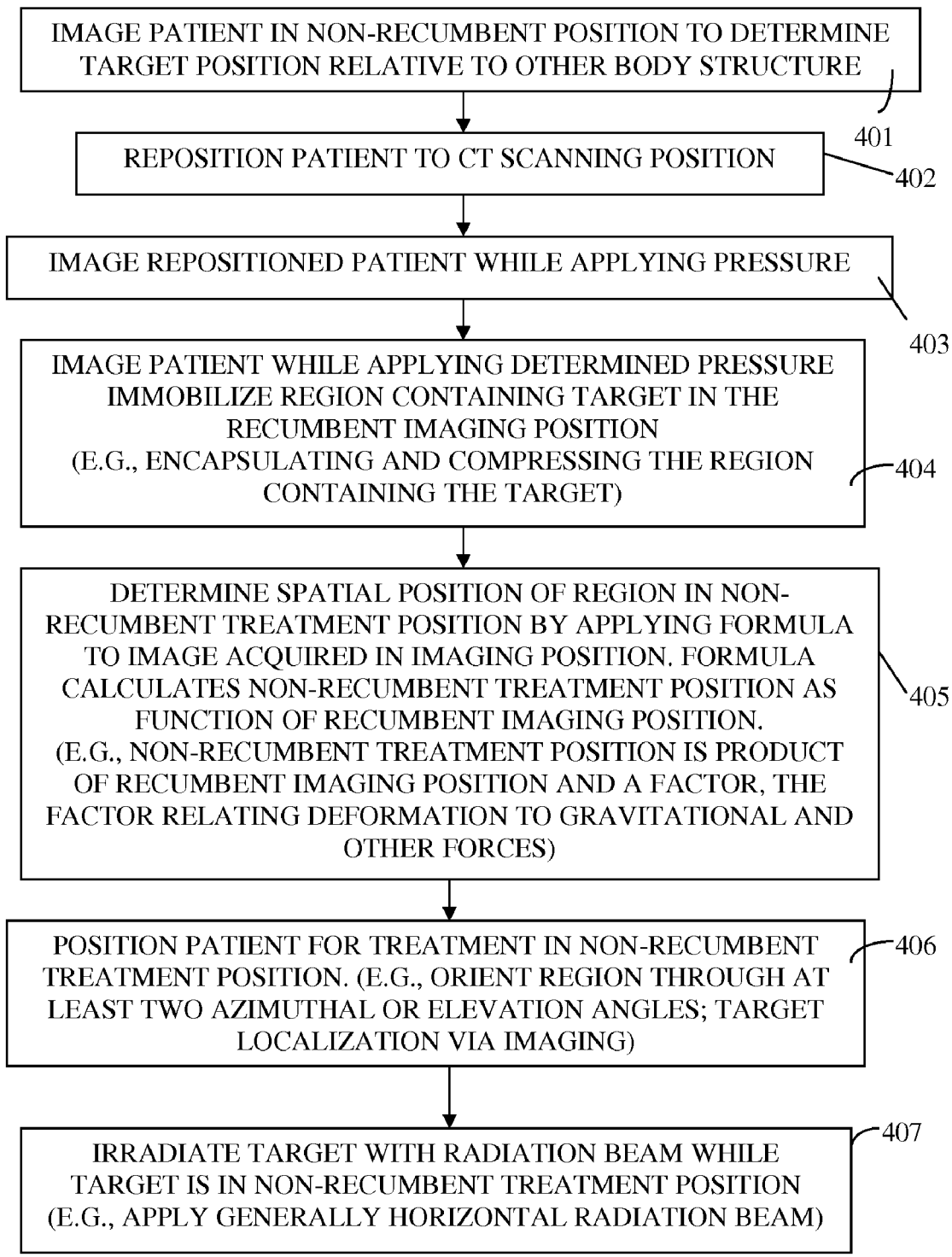
FIG. 4 is a simplified flow chart of a method for applying radiotherapy to a non-recumbent patient, in accordance with an embodiment of the present invention.

Reference is now made to FIG. 4, which illustrates a method for applying radiotherapy to a non-recumbent patient in accordance with an embodiment of the present invention. First, the patient may be imaged in the non-recumbent (e.g., upright) position to determine organ/tissue/target (referred to throughout the claims as the target) position relative to other body structure (e.g., bony structure) (step 401). The patient may then be repositioned to the CT scanning position (step 402). The repositioned patient may then be imaged while applying a pressure (step 403). The pressure applied is calculated as the pressure required for producing a position of the organ/tissue/target similar to that of the non-recumbent (e.g., upright) patient. The pressure is calculated with simplified formulas for deformation of bodies, and may take into account the tissue elasticity, discussed further below. The patient may then be imaged (e.g., CT-scanned) while applying the determined pressure (step 404).

In step 404, the region containing the target is immobilized in the recumbent imaging position. A spatial position of the region in the non-recumbent treatment position is determined by applying a formula to an image acquired in the imaging position, the formula calculating the non-recumbent treatment position as a function of the recumbent imaging position (step 405). The patient may then be positioned for treatment in the non-recumbent treatment position (step 406). The target may then be irradiated with a radiation beam while the target is in the non-recumbent treatment position (step 407).

Immobilizing the region in step 404 may include encapsulating and compressing the region containing the target. Positioning the patient in step 406 may include orienting the region through at least two azimuthal or two elevation angles. Additionally or alternatively, positioning the patient may include target localization via imaging.

Irradiating the target in step 407 may include applying a generally horizontal radiation beam.

The formula in step 405 may be based on a linear model, wherein the non-recumbent treatment position is a product of the recumbent imaging position and a factor, the factor relating deformation to gravitational and other forces.

Accordingly, in the present invention, image simulation for treatment planning is performed in the imaging position. The region containing the target is immobilized such that the region sensitivity to gravitational forces is reduced so that the associated deformation can be characterized by a simple formula. Such a characterization provides the ability to image the region in the imaging position and apply the formula to simulate a corresponding image in the non-recumbent treatment position.

In general, the model relating tissue deformation to applied (gravitational) force field is not necessarily linear. However, when the boundary conditions are fixed (by encapsulation) and tissue rigidity is significantly increased (by compression), the resulting deformation is small and a simplified (linear) model can be used. The model parameters can be derived, for example, from knowledge of the tissue mechanical parameters or by measuring the deformation related to different positions (with known gravitational forces) using adequate imaging equipment.

If it is desired to take tissue elasticity into account, the tissue elasticity can be either estimated (e.g., from previous testing, textbooks or other scientific literature) or measured. Methods for measuring and imaging tissue elasticity are described, for example, in U.S. Pat. Nos. 5,107,837, 5,293,870, 5,143,070 and 5,178,147 to Ophir et al., the disclosures of which are incorporated herein by reference. The methods include emitting ultrasonic waves along a path into the tissue and detecting an echo sequence resulting from the ultrasonic wave pulse. The tissue is then compressed (or alternatively decompressed from a compressed state) along the path and during such compression, a second pulse of ultrasonic waves is sent along the path into the tissue. The second echo sequence resulting from the second ultrasonic wave pulse is detected and then the differential displacement of selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions.

U.S. Pat. No. 5,265,612 to Sarvazyan et al., the disclosure of which is incorporated herein by reference, describes a device for elasticity imaging of the prostate using an ultrasonic transrectal probe. The device enables quantitative and objective characterization of elasticity moduli of prostate tissues.

In cases where the deformation is substantially eliminated, the formula is reduced to the identity relationship. This is the case, for example, with the compressed breast of FIGS. 3A and 3B: the patient may be imaged in a semi-prone position and treated in a semi-upright position while the breast substantially retains its shape in the two positions.

Extra-cranial organs may be initially only partially encapsulated. The pelvic region, for example, is only partially encapsulated by the pelvic bones while the breast is not naturally encapsulated at all. The applied pressure increases the rigidity and reduces the mobility of internal organs in the encapsulated region. In accordance with an embodiment of the invention, as described above, immobilizer 12 combines encapsulation and application of pressure to the encapsulated region.

The prostate and adjacent organs are pressed caudally by gravitation when a patient moves from a recumbent to an upright position. A similar effect may be produced by pressing the abdomen of a recumbent patient, thereby increasing the intra-abdominal pressure. The amount of pressure required to simulate gravitational organ displacement may be determined by imaging, such as but not limited to, X-ray, ultrasound or MRI. Applying pressure to the abdomen may be accomplished by attaching a balloon to the abdomen, wrapping around the patient and the balloon a wide belt and then inflating the balloon.

The scope of the present invention includes both combinations and subcombinations of the features described hereinabove as well as modifications and variations thereof which would occur to a person of skill in the art upon reading the foregoing description and which are not in the prior art.

What is claimed is:

1. A method for radiotherapy of a non-recumbent patient, comprising:
   immobilizing a region containing a target;
   determining a spatial position of the target in a non-recumbent treatment position by applying a formula to images acquired by recumbent-only imaging in a recumbent position and by general imaging in a non-recumbent position, the formula calculating the non-recumbent treatment position as a function of the target position relative to anatomical and/or other markers as calculated from recumbent-only imaging, and the position of the markers relative to a treatment device as calculated from general imaging in the non-recumbent position;
   positioning the patient for treatment in the non-recumbent treatment position according to the markers' position; and
   irradiating the target with a radiation beam while the target is in the non-recumbent treatment position.

2. The method according to claim 1, wherein immobilizing the region comprises encapsulating and compressing the region containing the target.

3. The method according to claim 1, wherein positioning the patient comprises orienting the region through at least two azimuthal or two elevation angles.

4. The method according to claim 1, wherein positioning the patient comprises target localization via imaging.

5. The method according to claim 1, wherein irradiating the target comprises applying a generally horizontal radiation beam.

6. The method according to claim 1, wherein the formula is based on a linear model, wherein the non-recumbent target position relates to the recumbent target position by a shift and a rotation determined by gravitational and other forces, wherein target position is relative to the markers.

7. The method according to claim 6, wherein for rigidly encapsulated regions, the shift and the rotation are minute.

8. The method according to claim 1, wherein the region is at least one of a pelvic region, a breast, and a skull.

9. A radiotherapy system for a non-recumbent patient comprising:
   an immobilizer operable to immobilize a region of tissue containing a target so that region deformation is characterized by a formula, wherein the region deformation is a relative position of the region of tissue in a recumbent position and in a non-recumbent position, respectively, and wherein said immobilizer comprises an inflatable balloon that when inflated immobilizes said region of tissue;
   an imaging device attachable to said immobilizer for imaging the target in a recumbent imaging position;
   a treatment device attachable to said immobilizer for performing treatment of the target in a non-recumbent position; and
   a processor operable to produce treatment simulation of the region in the non-recumbent position using the formula applied to an image acquired in the recumbent imaging position.

10. The system according to claim 9, wherein the immobilizer is operable to compress the region.

* * * * *